(12) United States Patent
Zhang et al.

(10) Patent No.: US 8,674,163 B2
(45) Date of Patent: Mar. 18, 2014

(54) DNA HYBRIDS AND ENVIRONMENT CLEANING SYSTEM EMPLOYING DNA HYBRIDS

(75) Inventors: Zuyi Zhang, Yokohama (JP); Teigo Sakakibara, Yokohama (JP); Yoshinori Kotani, Yokohama (JP); Norio Nishi, Sapporo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1218 days.

(21) Appl. No.: 11/653,233

(22) Filed: Jan. 16, 2007

(65) Prior Publication Data
US 2007/0135672 A1 Jun. 14, 2007

Related U.S. Application Data

(62) Division of application No. 10/535,894, filed as application No. PCT/JP2004/007472 on May 25, 2004, now abandoned.

(30) Foreign Application Priority Data

May 29, 2003 (JP) .................................. 2003-152619

(51) Int. Cl.
*A62D 3/33* (2007.01)
*A62D 3/00* (2007.01)
*C07H 21/02* (2006.01)
*C12Q 1/68* (2006.01)
*C12M 1/34* (2006.01)
*G01N 33/553* (2006.01)
*G01N 33/552* (2006.01)

(52) U.S. Cl.
USPC ........... 588/315; 588/405; 536/23.1; 435/6.1; 435/287.2; 436/525; 436/527

(58) Field of Classification Search
USPC .................... 588/315; 436/525, 527; 435/243
See application file for complete search history.

(56) References Cited

U.S. PATENT DOCUMENTS

| | | | | |
|---|---|---|---|---|
| 4,748,121 A | * | 5/1988 | Beaver et al. | 435/176 |
| 5,234,809 A | * | 8/1993 | Boom et al. | 435/91.2 |
| 6,303,290 B1 | | 10/2001 | Liu et al. | 435/4 |
| 6,811,980 B2 | | 11/2004 | Ford et al. | 435/6 |
| 6,838,005 B2 | | 1/2005 | Tepper et al. | 210/660 |
| 6,872,527 B2 | | 3/2005 | Gerdes et al. | 435/6 |
| 2004/0210289 A1 | | 10/2004 | Wang et al. | 607/116 |
| 2004/0254419 A1 | | 12/2004 | Wang et al. | 600/8 |
| 2005/0170402 A1 | | 8/2005 | Zhang et al. | 435/6 |
| 2006/0205007 A1 | | 9/2006 | Zhang et al. | 435/6 |

FOREIGN PATENT DOCUMENTS

| | | | |
|---|---|---|---|
| EP | 0 391 608 | 10/1990 | |
| EP | 0 391 608 A2 | 10/1990 | |
| JP | 2-286100 A | 11/1990 | |
| JP | 7-41494 | 2/1995 | |
| JP | 10-175994 | 6/1998 | |
| JP | 11-148935 | 6/1999 | |
| JP | 2001-81098 | 3/2001 | |
| JP | 2002-211954 | 7/2002 | |
| JP | 2002-218976 | 8/2002 | |
| WO | WO 9831840 A1 * | 7/1998 | |
| WO | WO 98131461 * | 7/1998 | B01J 20/28 |
| WO | 01/17667 | 3/2001 | |

OTHER PUBLICATIONS

Kathryn A. Melzak et al. "Driving Forces for DNA Adsorption to Silica in Perchlorate Solutions" Journal of Colloid and Interface Science 181, 635-644 (1996), Article No. 0421.*
Amendment to Specification in EP089556, Apr. 19, 2002 1 pg.*
Arthur T. Hubbard, "Encyclopedia of Surface and Colloid Science", vol. 3, Marcel Dekker, Inc., 2002, p. 3673.
Kazumichi Iwata, et al., "Utilization of DNA as functional materials: preparation of filters containing DNA insolubilized with alginic acid gel", International Journal of Biological Macromolecules, vol. 18, 1996, pp. 149-150.
Shou-Qing Liu, et al., "A reversible adsorption-desorption interface of DNA based on nano-sized zirconia and its application", Colloids and Surfaces B: Biointerfaces 36, 2004, pp. 155-159.
"Utilization of Salmon Milt DNA as a Functional Material", Material Report Review, vol. 19, No. 6, 1999, pp. 5-12.
Masanori Yamada, et al., "UV-Irradiated DNA Matrix Selectively Accumulates Heavy Metal Ions", Chemical Society of Japan, vol. 75, No. 7, 2002, pp. 1627-1632.
Masanori Yamada, et al., "UV-irradiation-induced DNA immobilization and functional utilization of DNA on nonwoven cellulose fabric", Biomaterials, vol. 22, 2001, pp. 3121-3126.
"colloid", The Columbia Electronic Encyclopedia, Sixth Edition, Columbia University Press, 2003, Answers.com Sep. 22, 2006, http://www.answers.com/topic/colloid.
"sol", The American Heritage Stedman's Medical Dictionary, Houghton Mifflin Company, 2002, Answers.com Sep. 22, 2006 http://www.answers.com/topic/sol-1.

* cited by examiner

*Primary Examiner* — Taeyoon Kim
*Assistant Examiner* — Srikanth Patury
(74) *Attorney, Agent, or Firm* — Fitzpatrick, Cella, Harper and Scinto

(57) ABSTRACT

A DNA hybrid which comprises a porous oxide matrix and DNA immobilized thereon, and is useful for environmental clean-up, where the hybrid is prepared by removing a dispersion medium from a dispersion of colloidal oxide and DNA.

4 Claims, No Drawings

DNA HYBRIDS AND ENVIRONMENT CLEANING SYSTEM EMPLOYING DNA HYBRIDS

This application is a divisional of application Ser. No. 10/535,894, which was the National Stage of International Application No. PCT/JP2004/007472, filed May 25, 2004. The contents of each of the foregoing applications is incorporated herein by reference.

TECHNICAL FIELD

The present invention relates to a DNA hybrid. More particularly, the invention relates to a DNA hybrid where DNA is immobilized firmly in an oxide matrix, having water resistance, retaining selective recognition function of DNA and allowing intercalation into the double helix of DNA. It also relates to an environmental clean-up system using this DNA hybrid.

BACKGROUND ART

DNA (deoxyribonucleic acid) carrying genetic information in living organisms is one of the most important materials for life process. DNA has the capability of extremely precise molecular-recognition, because DNA forms a double-stranded structure between two complementary strands via base pairs between them. Based on this principle, genetic diagnosis that uses the DNA chip has been developed. Application to biosensors and molecular devices is also expected. Also since the DNA double helix allows selective intercalation of an aromatic compound having a planar chemical structure, it is useful in removing a carcinogenic compound and the like, and is expected to be useful as an environmental cleaning material for removing a harmful substance in air or water (see FUNCTION & MATERIALS, Vol. 19, 1999).

For example, DNA chips carrying a lot of DNA fragments (DNA probes) on the surface of a substrate like a slide glass have been developed. Since DNA is naturally water-soluble, DNA must be immobilized onto the substrate for such applications. In order to immobilize a biological substance on a substrate, organic crosslinking reaction is conventionally utilized. For instance, there is a method of supporting a biological substance such as nucleic acid, protein and peptide on the roughened surface of a slide glass having a surface layer of a carbon-based material (see Japanese Patent Application Laid-open No. 2002-211954). In this method, first the carbon surface is carboxylized and subjected to dehydration-polycondensation with carbodiimide and N-hydroxysuccinimide to form active ester groups such as N-hydroxysuccinimide ester group on the end of the hydrocarbons through an amide bond, and then the biological substance to be supported is bonded to the activated surface. Also a method and a kit for quantitatively detecting nucleic acid are disclosed in Japanese Patent Application Laid-open No. H11-148935.

Furthermore, a method for immobilizing nucleic acid on a substrate is disclosed where the substrate is activated by using atomic-oxygen plasma to immobilize nucleic acid thereon (see Japanese Patent Application Laid-open No. 2002-218976). Any one of these technologies has such problems that the supporting region is limited to the surface of the substrate and the process is complicated.

In addition to the organic crosslinking reaction, a crosslinking reaction with a metal ion was also proposed. Japanese Patent Application Laid-open No. H7-41494 discloses a method for immobilizing a deoxyribonucleic acid by coagulating an alkaline metal salt of the deoxyribonucleic acid and an alkaline metal salt of alginic acid using a divalent metal-containing compound.

Meanwhile, concerning the use of DNA as an environmental cleaning material, Japanese Patent Application Laid-open No. 2001-81098 proposes a material where DNA is solidified and immobilized on a support by irradiating UV light of 250 to 270 nm to a liquid film or thin layer of water-soluble DNA on the support. Further, Japanese Patent Application Laid-open No. H10-175994 discloses a DNA complex where DNA is immobilized on an inorganic solid. In these methods DNA is crosslinked to develop water resistance, but there are such problems that the exposed area of DNA is small and functions of DNA are not developed efficiently.

U.S. Pat. No. 6,303,290 discloses a method for immobilizing a biological material on a matrix of silica colloid. In this method, although the matrix has a large number of micropores, the matrix strength is not enough.

DISCLOSURE OF THE INVENTION

The DNA carriers obtained by the above methods are not adequate as a DNA composite material applicable to selective absorption process or environmental clean-up with high efficiency, in view of the DNA-supporting strength and function expression. The present invention has been made to solve such problems in the prior arts, and an object of the present invention is to provide a DNA hybrid where DNA is effectively immobilized and exhibits sufficient function, a preparing method therefor, and further an environmental clean-up system using the DNA hybrid.

The invention includes the following aspects.

(1) A DNA hybrid which comprises a porous oxide matrix and a DNA immobilized on the matrix, where the DNA hybrid is characterized by that it is prepared by removing a dispersion medium from a dispersion of a colloidal oxide and DNA.

(2) The DNA hybrid described in the above (1) characterized in that the dispersion medium is removed by heating the dispersion at 25° C. to 200° C.

(3) The DNA hybrid described in the above (1), characterized in that the DNA content in the hybrid is 0.01 to 15% by mass.

(4) The DNA hybrid described in the above (1) or (3), characterized in that the colloidal oxide is a mixture of a colloidal silica and at least one colloidal oxide of a metal whose valence is 3 or 4.

(5) The DNA hybrid described in the above (1), characterized in that the oxide comprises at least one oxide selected from the group consisting of aluminum oxide, iron oxide, titanium oxide and zirconium oxide.

(6) A method for producing a DNA hybrid which comprises the steps of preparing a dispersion comprising a colloidal oxide, a DNA and a dispersion medium; and removing the dispersion medium from the dispersion to immobilize the DNA in a porous matrix made of the oxide.

(7) The method described in the above (6), characterized in that the dispersion medium is removed by heating the dispersion at 25° C. to 200° C.

(8) The method described in the above (6), characterized in that the DNA content of the DNA hybrid is 0.01 to 15% by mass.

(9) The method described in the above (6) or (8), characterized in that the colloidal oxide is a mixture of colloidal silica and at least one colloidal oxide of a metal whose valence is 3 or 4.

(10) The method described in the above (9), characterized in that the oxide comprises at least one oxide selected from the group consisting of aluminum oxide, iron oxide, titanium oxide and zirconium oxide.

(11) An environmental cleaning system for removing a harmful substance in water, which comprises a DNA hybrid described in the above (1) and means for bringing the DNA hybrid into contact with a water containing a harmful substance.

(12) An environmental cleaning method by removing a harmful substance in a water, characterized in that a DNA hybrid described in the above (1) is brought into contact with water containing a harmful substance to adsorb the harmful substance by the DNA hybrid.

BEST MODE FOR CARRYING OUT THE INVENTION

In the invention, colloid aggregation or gelling occurs in the DNA containing oxide colloid dispersion as of the dispersion medium is evaporated or because of the presence of a third component, and finally a porous oxide gel is formed after the dispersion medium is removed. DNA is taken in the oxide colloid during stages from dispersion to gellation to be immobilized in the porous matrix.

DNA employed in the invention is not limited particularly for its size or type, provided that it achieves the purpose of use when being immobilized in the matrix. Such DNA may be single-strand or double-stranded DNA obtained from, for instance, soft roe or animal thymus; preferably obtained from soft roe (testis) of salmon, herring or cod; and also preferably obtained from the thymus of mammals or birds such as cow, pig and chicken.

Other example of water-soluble DNA may be a synthetic DNA, for instance, poly (dA)-poly (dT) having base pairs of (dA)-(dT). The molecular weight of DNA is preferably 100,000 or higher, more preferably 500,000 or higher.

The content (by mass) of DNA in the DNA hybrid according to the present invention is in a range of 0.01 to 15% and preferably of 0.1 to 10%. DNA content of 0.01% or more enables sufficient expression efficacy of DNA-originated properties, and DNA content of 15% or less can obviate the cost efficiency problem and allow formation of pores in the DNA hybrid. The pores allow rapid movement of gas and liquid into the DNA hybrid, so that DNA can achieve its function not only on the surface but also in the pores.

The colloidal oxide employed in the invention may be, for example, colloidal silica, colloidal aluminum oxide, colloidal iron oxide, colloidal gallium oxide, colloidal lanthanum oxide, colloidal titanium oxide, colloidal cerium oxide, colloidal zirconium oxide, colloidal tin oxide, colloidal hafnium oxide and the like. Any of these can be used alone or in combination of two or more. In view of the matrix stability and the cost, it is preferred to use readily available silica colloid as the main matrix component. More preferably, colloidal silica is used in combination with at least one colloidal oxide of trivalent or tetravalent metal. Addition of colloidal oxide of tri- or tetravalent metal causes binding between the phosphate group of DNA and the metal ion, which enhances the DNA-holding ability of the matrix, preventing elution of DNA in the ordinary aqueous environment. As a solid in the colloid, the 3- or 4-valent metal oxide content is preferably 0.1 to 50% by mass. Among those listed above, iron oxide, titanium oxide and zirconium oxide are especially preferred. Any of these colloids can be synthesized by the hydrothermal reaction. Alternatively, an aqueous colloidal dispersion of oxide is commercially available.

Examples of colloidal silica include aqueous sols such as SNOWTEX 20, SNOWTEX 30, SNOWTEX N, SNOWTEX O, SNOWTEX C (trade names, provided by NISSAN CHEMICAL INDUSTRIES, LTD.) and the like, methanolic sols, and solvent-based sols such as IPA-ST, EG-ST, MEK-ST (trade name, provided by NISSAN CHEMICAL INDUSTRIES, LTD.), OSCAL-1132, OSCAL-1432, OSCAL-1232 (trade name, provided by SHOKUBAI KASEI KOGYO). Examples of colloidal aluminum oxide are those marketed by NISSAN CHEMICAL INDUSTRIES, LTD. under the trade name of ALUMINA SOL 100, ALUMINA SOL 520 and the like.

To immobilize DNA in the oxide matrix, first a mixture of a DNA solution and a colloidal oxide dispersion is prepared and the dispersion medium is removed from the mixture. The surface of colloidal oxide particles may be modified in advance to prevent agglomeration of colloid particles in the dispersion stage. The modification can be accomplished by adding a chelating agent such as a surfactant, titanium compound, silane coupling agent, β-diketone and the like and an organic acid such as acetic acid as appropriate to a colloidal dispersion to partially modify the surface of the colloid particles. The colloidal dispersion thus obtained was combined with an aqueous solution of DNA to obtain a DNA hybrid. In the step of immobilization, the dispersion medium is removed by means of heating, spray drying, vacuum drying and the like to form an oxide matrix. A drying process with heating is especially preferred because it enhances the matrix strength. The temperature of heat treatment for DNA hybrid is preferably 25° C. or higher and 200° C. or lower, more preferably not lower than 30° C. and not higher than 150° C. If necessary, a third component may be added to strengthen the bond between the oxide colloid particles. The third component is not limited particularly, including acid or base, water-soluble metal compound and metal alkoxide that can promote the aggregation of colloid particles.

The DNA hybrid may be used in a form of powder or bulk. In addition, it may be used as a coating film on a substrate such as plate, tube, fiber, woven fabric and non-woven fabric, as needed. Accordingly, the DNA hybrid according to the present invention can be used in these forms. For instance, DNA hybrid powder can be obtained by spray drying of a dispersion containing colloidal oxide and DNA. Alternatively, first DNA hybrid is formed in the bulk and then the bulk is pulverized.

Furthermore, it is possible to make a module using the above-described DNA hybrid powder, or plate, tube, fiber, woven or non-woven fabric to which DNA hybrid is immobilized. For instance, a column filled with the DNA hybrid powder can be used for extracting a specific substance from a gas or a liquid. Or a filter module may be contemplated using a fiber or fabric supporting the DNA hybrid to filter cow's milk or mother's milk.

Such a module can be applied to an environmental clean-up system for removing hazardous materials from various effluents, waste water, and river or lake water. For instance, as described above, a column containing the DNA hybrid powder, or DNA hybrid held on a plate, a tube, a fiber, a woven or non-woven fabric can be used to purify water containing a harmful substance by passing it through the column.

EXAMPLES

Example 1

Five parts by mass of double-stranded DNA obtained from salmon testis (molecular weight: $6\times10^6$) was dissolved in 1000 parts by mass of ion exchange water over a day to obtain an aqueous solution of DNA.

To 70 parts by mass of 30% silica sol (NISSAN CHEMICAL INDUSTRIES, LTD., SNOWTEX CM), 20 parts by mass of 20% by mass alumina sol (NISSAN CHEMICAL INDUSTRIES, LTD., ALUMINA SOL 520) was added with stirring. The resultant sol mixture was combined with 100 parts by mass of the DNA solution, and stirred slowly for 10 minutes. Subsequently, the resultant DNA dispersion was dried for 24 hours at 50° C. to obtain DNA Hybrid 1 whose DNA content was about 2% by mass.

This DNA hybrid was subjected to an elution test. To 20 parts by mass of ion-exchanged water, 0.05 parts by mass of the DNA hybrid powder was added and settled in a sealed condition at room temperature for 48 hours. The absorbance (260 nm) of DNA in the supernatant liquid measured by a spectrophotometer (U-3310, Hitachi) was 0.05 or less. The DNA hybrid was proved to be holding 95 mass % or more of the DNA. When 0.5 parts by mass of the DNA hybrid was put into an aqueous solution of 60 ppm ethidium bromide, the DNA hybrid turned red after three hours, while the red color due to ethidium bromide in the supernatant decreased. When irradiated with ultraviolet light of 366 nm wavelength, the DNA hybrid emitted an orange fluorescence, which ensured that the intercalating function for a hazardous compound having a planar structure was maintained.

The DNA hybrid showed a specific surface area of 135 $m^2/g$, when measured with a nitrogen adsorption method.

Example 2

To 70 parts by mass of 30% silica sol (NISSAN CHEMICAL INDUSTRIES, LTD., SNOWTEX CM), 40 parts by mass of 20% by mass alumina sol (NISSAN CHEMICAL INDUSTRIES, LTD., ALUMINA SOL 520) was added with stirring. The resultant sol mixture was combined with 100 parts by mass of the DNA solution prepared in Example 1, and stirred slowly for 10 minutes. Subsequently, the resultant DNA dispersion was dried for 24 hours at 50° C. to obtain DNA Hybrid 2 whose DNA content was about 1.7% by mass.

This DNA hybrid was subjected to an elution test. To 20 parts by mass of ion-exchanged water, 0.05 parts by mass of the DNA hybrid powder was added and settled in a sealed condition at room temperature for 48 hours. The absorbance (260 nm) of DNA in the supernatant liquid measured by a spectrophotometer (U-3310, Hitachi) was about 0.02. The DNA hybrid was proved to be holding 98 mass % or more of the DNA.

Example 3

To 70 parts by mass of 30% silica sol (NISSAN CHEMICAL INDUSTRIES, LTD., SNOWTEX CM), 60 parts by mass of a titanium oxide sol (TAKI CHEMICAL CO., LTD., M-6, 6% by mass) was added with stirring. The resultant sol mixture was combined with 100 parts by mass of the DNA solution prepared in Example 1, and stirred slowly for 10 minutes. Subsequently, the resultant DNA dispersion was dried for 24 hours at 50° C. to obtain DNA Hybrid 3 whose DNA content was about 1% by mass.

This DNA hybrid was subjected to an elution test. To 20 parts by mass of ion-exchanged water, 0.1 parts by mass of the DNA hybrid powder was added and settled in a sealed condition at room temperature for 48 hours. The absorbance (260 nm) of DNA in the supernatant liquid measured by a spectrophotometer (U-3310, Hitachi) was about 0.05. The DNA hybrid was proved to be holding 95 mass % of the DNA.

Example 4

To 70 parts by mass of 30% silica sol (NISSAN CHEMICAL INDUSTRIES, LTD., SNOWTEX CM), 100 parts by mass of a titanium oxide sol (TAKI CHEMICAL CO., LTD., M-6, 6% by mass) was added with stirring. The resultant sol mixture was combined with 100 parts by mass of the DNA solution prepared in Example 1, and stirred slowly for 10 minutes. Subsequently, the resultant DNA dispersion was dried for 24 hours at 50° C. to obtain DNA Hybrid 4 whose DNA content was about 1.8% by mass.

This DNA hybrid was subjected to an elution test. To 20 parts by mass of ion-exchanged water, 0.1 parts by mass of the DNA hybrid powder was added and settled in a sealed condition at room temperature for 48 hours. The absorbance (260 nm) of DNA in the supernatant liquid measured by a spectrophotometer (U-3310, Hitachi) was about 0.07. The DNA hybrid was proved to be holding 96 mass % of the DNA.

Example 5

To 100 parts by mass of 30% silica sol (NISSAN CHEMICAL INDUSTRIES, LTD., SNOWTEX CM), 50 parts by mass of a titanium oxide sol (TAKI CHEMICAL CO., LTD., M-6, 6% by mass) was added with stirring. The resultant sol mixture was combined with 20 parts by mass of the DNA solution prepared in Example 1, and stirred slowly for 10 minutes. Subsequently, the resultant DNA dispersion was dried for 24 hours at 50° C. to obtain DNA Hybrid 5 whose DNA content was about 0.3% by mass.

This DNA hybrid was subjected to an elution test. To 20 parts by mass of ion-exchanged water, 0.1 parts by mass of the DNA hybrid powder was added and settled in a sealed condition at room temperature for 48 hours. The absorbance (260 nm) of DNA in the supernatant liquid measured by a spectrophotometer (U-3310, Hitachi) was not detected. The DNA hybrid was proved to be holding almost all DNA.

Comparative 1

Parts by mass of a silica powder whose particle size was 0.063 to 0.2 mm was combined with 5.6 parts by mass of the DNA solution of Example 1 and mixed uniformly. The resultant paste was dried for 24 hours at 50° C. to obtain a silica powder whose DNA supporting level was 0.56% by mass. 0.040 Parts by mass of the resultant silica powder was combined with 5 parts by mass of ion exchange water to conduct the elution test. The absorbance of the supernatant at 260 nm was 0.56. Thus, it was revealed that about 61% by mass of the DNA was eluted.

The present invention is not limited to the above embodiments and various changes and modifications can be made within the spirit and scope of the present invention. Therefore to apprise the public of the scope of the present invention, the following claims are made.

The invention claimed is:

1. A method for producing a DNA hybrid comprising the steps of:
   preparing a dispersion comprising colloidal silica, at least one colloidal metal oxide which comprises an oxide of a metal with a valence of 3 or 4, and a DNA, wherein the colloidal silica and the at least one colloidal metal oxide are separate components of the dispersion; and
   gelling the dispersion by heating to immobilize the DNA in a porous matrix made by gellation of the colloidal silica and the at least one colloidal metal oxide,
   wherein the content of the 3- or 4-valent metal oxide is 0.1 to 50% by mass relative to the total mass of the colloidal silica and the at least one colloidal metal oxide.

2. The method according to claim 1, wherein the gellation of the colloidal silica and the at least one colloidal metal oxide is effected by removing a dispersion medium by heating the dispersion at 25° C. to 200° C.

3. The method according to claim 1, wherein the content of the DNA is 0.01 to 15% by mass relative to the total mass of the DNA hybrid.

4. The method according to claim 1, wherein the at least one colloidal metal oxide comprises at least one oxide selected from the group consisting of aluminum oxide, iron oxide, titanium oxide and zirconium oxide.

* * * * *